United States Patent
Cain et al.

(10) Patent No.: US 6,413,216 B1
(45) Date of Patent: Jul. 2, 2002

(54) METHOD AND ASSEMBLY FOR PERFORMING ULTRASOUND SURGERY USING CAVITATION

(75) Inventors: Charles A. Cain; J. Brian Fowlkes, both of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/470,644

(22) Filed: Dec. 22, 1999

Related U.S. Application Data

(63) Continuation-in-part of application No. 09/218,310, filed on Dec. 22, 1998.

(51) Int. Cl.[7] ................................................ A61B 8/00
(52) U.S. Cl. ........................... 600/439; 601/2; 424/9.5; 424/9.51; 424/9.52; 424/450
(58) Field of Search .............. 600/439; 601/2, 601/24; 604/22; 424/450, 9.5, 9.51, 9.52

(56) References Cited

U.S. PATENT DOCUMENTS

| | | |
|---|---|---|
| 4,689,986 A | 9/1987 | Carson et al. |
| 5,215,680 A | 6/1993 | D'Arrigo |
| 5,219,401 A | 6/1993 | Cathignol et al. |
| 5,435,311 A | 7/1995 | Umemura et al. |
| 5,474,531 A | 12/1995 | Carter |
| 5,540,909 A | 7/1996 | Schutt |
| 5,542,935 A | 8/1996 | Unger et al. |
| 5,558,092 A | 9/1996 | Unger et al. |
| 5,573,497 A | 11/1996 | Chapelon |
| 5,580,575 A | 12/1996 | Unger et al. |
| 5,582,578 A | 12/1996 | Zhong et al. |

(List continued on next page.)

FOREIGN PATENT DOCUMENTS

| | | |
|---|---|---|
| EP | 0 332 871 | 2/1989 |
| EP | 0 384 831 | 2/1990 |
| WO | WO 94/06355 | 3/1994 |

OTHER PUBLICATIONS

Thomas R. Porter, et al., "Reduction in Left Ventricular Cavitary Attenuation and Improvement in Posterior Myocardial Contrast with Higher Molecular Weight Intravenous Perfluorocarbon–Exposed Sonicated Dextrose Albumin Microbubbles", Journal of American Society of Echocardiography, Jul.–Aug. 1996, pp. 437–441.

*Primary Examiner*—George Manuel
*Assistant Examiner*—Runa Shah Qaderi
(74) *Attorney, Agent, or Firm*—Brooks & Kushman P.C.

(57) ABSTRACT

A method and assembly are provided which use cavitation induced by an ultrasound beam for creating a controlled surgical lesion in a selected treatment volume of a patient, such as an internal body cavity or organ. First, a plurality of microbubbles are provided in the treatment volume. Preferably, the threshold for cavitation of microbubbles in the treatment volume is lowered compared with the threshold for cavitation in surrounding tissues. The expected location of the surgical lesion within the treatment volume may be previewed, and then the microbubbles in the treatment volume are cavitated with the ultrasound beam to create the controlled surgical lesion. In addition, substances can be associated with the microbubbles such that cavitation of the microbubbles delivers the substances to the treatment volume. Preferably, the creation of the surgical lesion at the expected lesion location is then verified. Using the method and assembly of the present invention, the cavitation threshold within the treatment volume is made predictable, and a low frequency ultrasound beam may be used to cavitate the microbubbles within the treatment volume without causing damage to surrounding tissues.

44 Claims, 4 Drawing Sheets

U.S. PATENT DOCUMENTS

| | | |
|---|---|---|
| 5,590,657 A | 1/1997 | Cain et al. |
| 5,601,526 A | 2/1997 | Chapelon et al. |
| 5,648,098 A | 7/1997 | Porter |
| 5,676,692 A | 10/1997 | Sanghvi et al. |
| 5,694,936 A | 12/1997 | Fujimoto et al. |
| 5,770,222 A | 6/1998 | Unger et al. |
| 5,827,204 A | 10/1998 | Grandia et al. |
| 5,836,896 A | 11/1998 | Rosenschein |
| 5,849,727 A * | 12/1998 | Porter et al. .......... 514/156 |
| 5,947,904 A | 9/1999 | Hossack et al. |
| 6,088,613 A | 7/2000 | Unger |
| 6,176,842 B1 | 1/2001 | Tachibana et al. |

* cited by examiner

METHOD AND ASSEMBLY FOR PERFORMING ULTRASOUND SURGERY USING CAVITATION

CROSS-REFERENCE TO RELATED APPLICATIONS

This application is a continuation-in-part of U.S. application Ser. No. 09/218,310 filed Dec. 22, 1998.

TECHNICAL FIELD

This invention relates to ultrasound surgery, and more particularly to a method and assembly for the controlled use of cavitation during diagnostic and therapeutic ultrasound procedures.

BACKGROUND ART

Chronic excessive bleeding of the endometrium of the uterus, termed endometriosis, is thought to have a genetic basis in many patients and is estimated to afflict 15% of women in their reproductive years. Heat cauterization of uterine blood vessels has been attempted as a means to treat endometriosis, wherein a hot fluid filled balloon is inserted through the cervix and then inflated to contact the uterine interior. However, this approach has trouble reaching all the internal folds of the uterus, and heat cauterization provides only partial and short-lived benefits. The predominant method for the treatment of endometriosis, as well as uterine fibroid tumors and related gynecological disorders involves the surgical removal of uterine cells or complete hysterectomy, both of which are invasive means of removing pathological uterine tissues. These methods leave scars or other disfigurements which can be both physically and psychologically debilitating.

Compared with other surgical methods, a primary advantage of ultrasound surgery is its noninvasive nature. Ultrasound allows diagnostic and therapeutic procedures to be accomplished either wholly from means external to the body, or with minimal dependence on procedures no more invasive than current laproscopic techniques. Being noninvasive, the cost advantages, both in hospital stay and in surgical preparation time, are readily apparent. In addition, the lack of cosmetic disfigurement and risk of infection are both significant advantages for ultrasound procedures.

Ultrasound can be utlized for diagnostic imaging, where an ultrasound transducer is used to generate ultrasonic waves which are directed at a region of interest in a patient. The transducer then receives reflected ultrasonic waves from the region and converts the received waves into electrical signals from which an image is generated. Ultrasound has also been used in various therapeutic applications. One such application, thermally-based ultrasound surgery, involves applying ultrasonic waves to a targeted treatment volume, such as a tumor, in order to heat the treatment volume and create a lesion. An example of such an application can be found in U.S. Pat. No. 5,694,936 issued to Fujimoto et al. Another application of therapeutic ultrasound is in the treatment of vascular thrombosis as seen, for example, in U.S. Pat. No. 5,648,098 issued to Porter. Unfortunately, the otherwise beneficial results of both diagnostic and therapeutic ultrasound procedures are often made unpredictable by the phenomenon of acoustic cavitation.

Acoustic cavitation is a term used to define the interaction of an acoustic field, such as an ultrasound field, with bodies containing gas and/or vapor. This term is used in reference to the production of small gas bubbles, or microbubbles, in the liquid. Specifically, when an acoustic field is propagated into a fluid, the stress induced by the negative pressure produced can cause the liquid to rupture, forming a void in the fluid which will contain vapor and/or gas. Acoustic cavitation also refers to the oscillation and/or collapse of microbubbles in response to the applied stress of the acoustic field.

The induced oscillation of microbubbles can generally be categorized as noninertial cavitation or as inertial cavitation. Noninertial cavitation appears at very low acoustic pressure amplitudes, as soon as microbubbles are present in a tissue. In noninertial cavitation, the walls of the microbubbles oscillate at the frequency of the ultrasound field generally without damaging surrounding cells, but considerably disturbing ultrasound transmission by reflecting or scattering incident waves. Inertial cavitation appears rather suddenly at higher incident pressures, defining a cavitation onset threshold. In inertial cavitation, microbubbles expand to reach a critical size after which the collapse is driven by the inertia of the surrounding fluid, thus the term "inertial" cavitation. Microbubble size is a determining factor in the degree of response to the ultrasound field, such that microbubbles are highly resonant oscillators at certain drive frequencies. Microbubble oscillation can be sufficiently violent to produce mechanical or thermal damage on surrounding tissue, thereby creating lesions.

In current practice, significant steps are usually taken to avoid cavitation, as described in U.S. Pat. No. 5,573,497 issued to Chapelon. Typically, cavitation is only permitted where it can be very carefully controlled and localized, such as at the end of a small probe or catheter as in U.S. Pat. No. 5,474,531 issued to Carter. The primary reason for avoiding cavitation is that thresholds for inducing cavitation of microbubbles are unpredictable due to the diversity of microbubble sizes and quantities in different tissues. Uncontrolled cavitation hinders the penetration of ultrasonic waves into tissue, and can lead to uncontrolled tissue destruction outside the intended treatment volume. As a result, surgical protocols have been formulated which attempt to increase cavitation onset thresholds in most diagnostic and therapeutic applications.

Cavitation occurs more easily at low frequencies of ultrasound transmission, with the cavitation threshold increasing as the frequency of ultrasonic waves is increased. Therefore, the predominant method of controlling cavitation during ultrasound procedures has been to utilize high frequency ultrasonic waves, as disclosed, for example, in U.S. Pat. No. 5,601,526 issued to Chapelon et al. and in U.S. Pat. No. 5,558,092 issued to Unger et al. However, this approach is not without drawbacks, as high frequency ultrasound cannot penetrate as far in soft tissue or through bone. In addition, high frequency ultrasound often has the detrimental effect of excessively heating tissues located between the ultrasound transducer and the intended treatment volume.

DISCLOSURE OF INVENTION

Contrary to past approaches, it is an object of the present invention to provide a method and assembly for performing ultrasound surgery which uses, instead of avoids, cavitation for diagnostic and therapeutic ultrasound procedures.

It is a further object of the present invention to provide a method and assembly for performing ultrasound surgery which makes cavitation thresholds predictable.

It is another object of the present invention to provide a method and assembly for performing ultrasound surgery which creates a controlled lesion within an intended treatment volume.

It is a further object of the present invention to provide a method and assembly for performing ultrasound surgery which utilizes low frequency ultrasonic waves to create the lesion.

It is another object of the present invention to provide a method and assembly for performing ultrasound surgery which allows for a preview of the expected lesion location within a treatment volume.

It is yet another object of the present invention to provide a method and assembly for performing ultrasound surgery which allows verification of proper lesion formation within the treatment volume.

It is a further object of the present invention to provide a method and assembly for performing ultrasound surgery in which substances associated with the microbubbles can be delivered within the treatment volume.

Accordingly, a method and assembly are provided which use cavitation induced by an ultrasound beam for creating a controlled surgical lesion in a selected treatment volume of a patient. First, a plurality of microbubbles are provided in the treatment volume. Preferably, the threshold for cavitation of microbubbles in the treatment volume is lowered compared with the threshold for cavitation in surrounding tissues. The expected location of the surgical lesion within the treatment volume may be previewed, and then the microbubbles in the treatment volume are cavitated with the ultrasound beam to create the controlled surgical lesion. In addition, substances such as drugs or DNA can be associated with the microbubbles such that cavitation of the microbubbles delivers the substances to the treatment volume. Preferably, the creation of the surgical lesion at the expected lesion location is then verified. Using the method and assembly of the present invention, the cavitation threshold within the treatment volume is made predictable, and a low frequency ultrasound beam may be used to cavitate the microbubbles within the treatment volume without causing damage to surrounding tissues.

The above objects and other objects, features, and advantages of the present invention are more readily understood from a review of the attached drawings and the accompanying specification and claims.

BEST MODE FOR CARRYING OUT THE INVENTION

Figure 1:
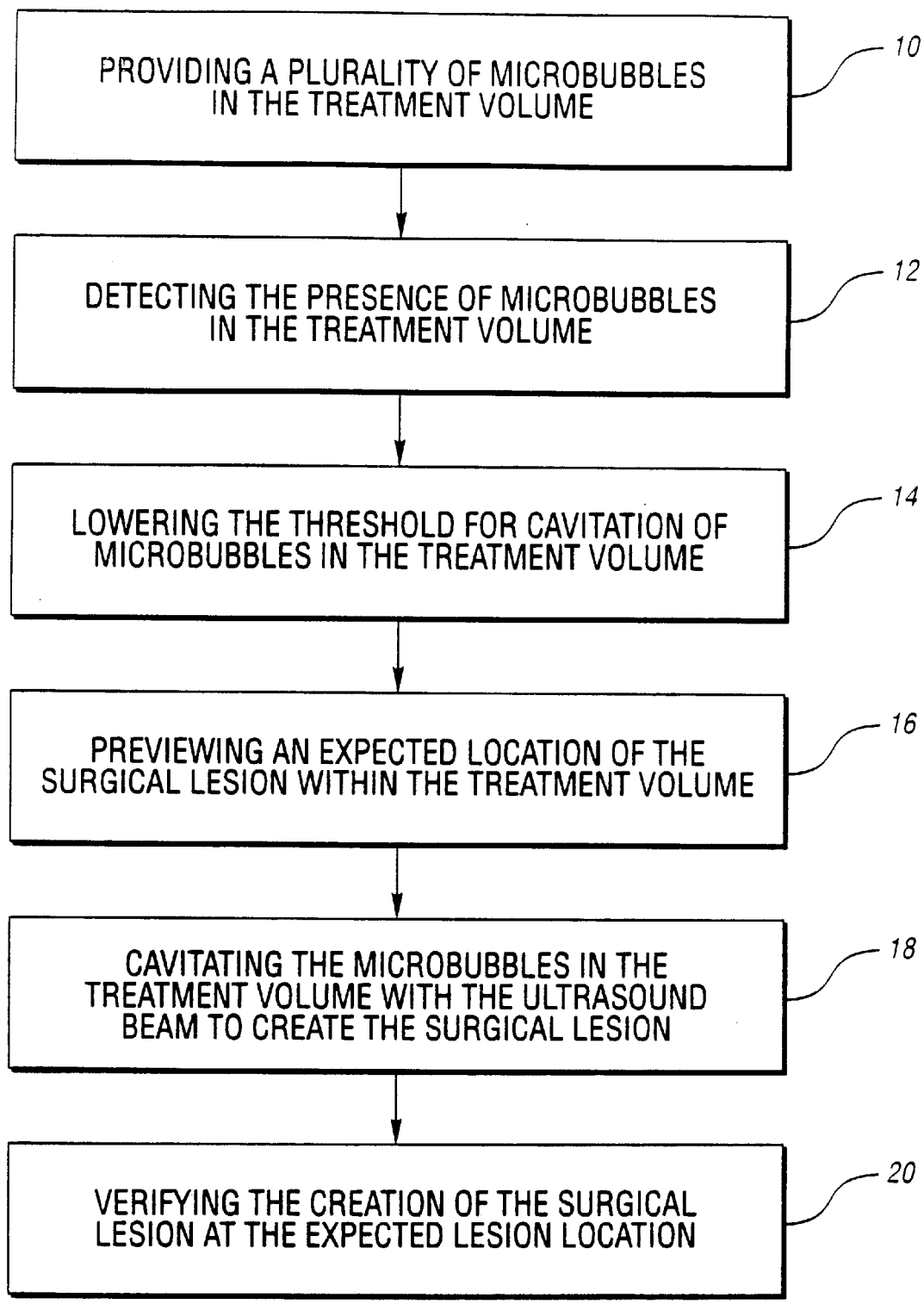
FIG. 1 is an outline of the method of the present invention.

The method and assembly of the present invention use cavitation induced by an ultrasound beam to create a controlled surgical lesion in a selected treatment volume of a patient. One such treatment volume includes the internal surfaces of body cavities or organs, where the primary targets of interest would be the uterus and bladder. Of course, other organs such as the stomach, intestines, lungs, and blood vessels, for example, could also be treated as described herein. In overview, as outlined in FIG. 1, the method comprises providing 10 a plurality of microbubbles in the treatment volume, and then subsequently the presence of microbubbles may be detected 12 in the treatment volume. Preferably, the threshold for cavitation of microbubbles in the treatment volume is then lowered 14 compared with cavitation thresholds outside the treatment volume. The expected location of the surgical lesion within the treatment volume maybe previewed 16, and then the microbubbles in the treatment volume are cavitated 18 with the ultrasound beam to create the controlled surgical lesion. Preferably, the creation of the surgical lesion at the expected lesion location is then verified 20. This method, which is described in greater detail below, is carried out using a combined therapeutic and diagnostic ultrasound assembly 22 as shown in FIG. 2.

Figure 2:
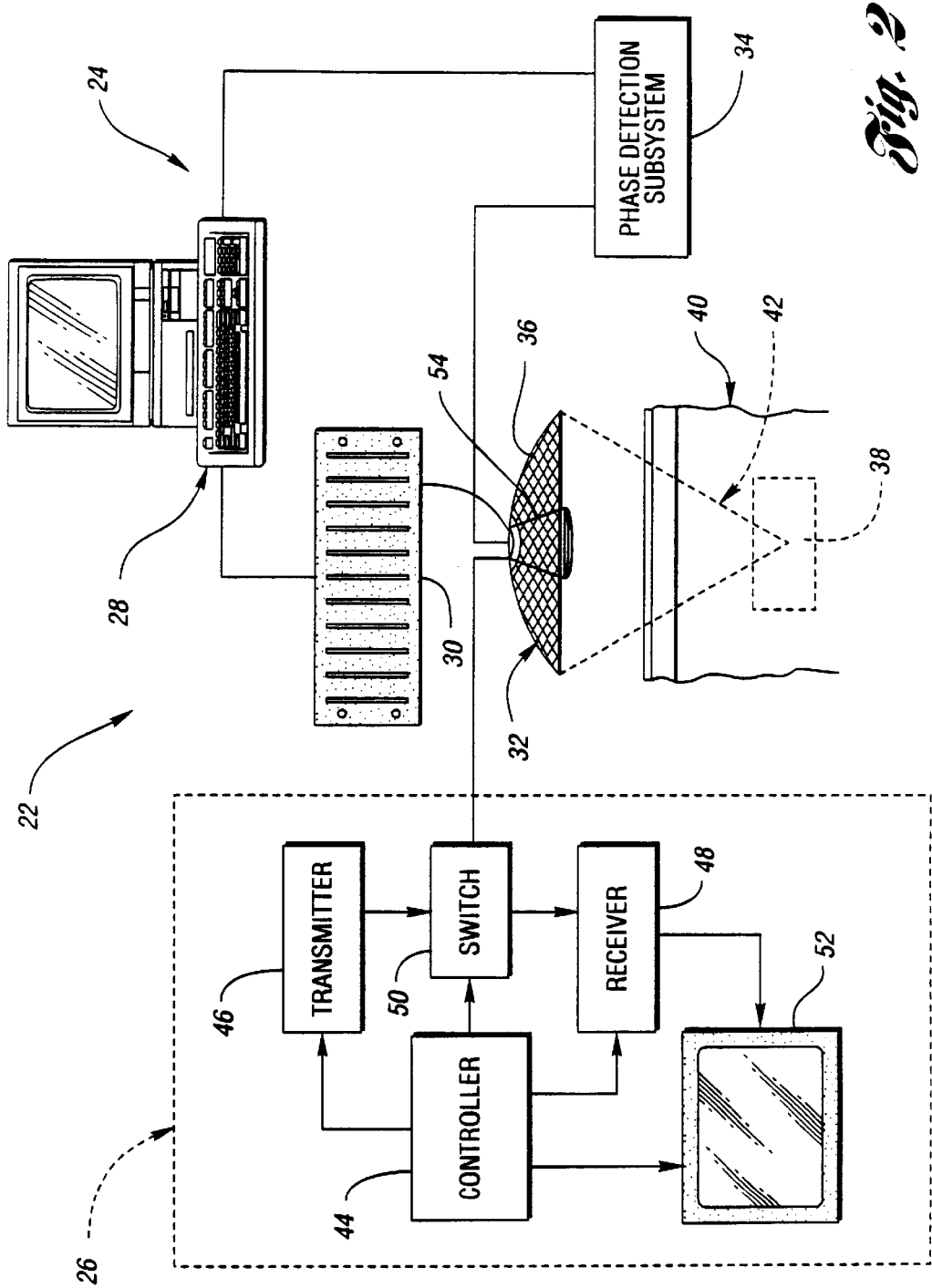
FIG. 2 is a schematic illustration of an ultrasound assembly utilized in the method of the present invention.

FIG. 2 shows an ultrasound assembly 22 in accordance with the present invention which includes a therapeutic ultrasound system 24 and a diagnostic ultrasound system 26. To produce cavitation, therapeutic ultrasound system 24 can include one or more large aperture, unfocused transducers operating at low frequency where depth of propagation is large and unwanted heating effects are minimal. These transducers could be external transducers or internal, intracavity transducers (e.g. intravaginal, intrauterine, transrectal). In a preferred embodiment, therapeutic ultrasound system 24 is a phased array ultrasound system which generally includes a microprocessor-based controller 28, a network of drivers 30, an ultrasound array 32, and a phase detection subsystem 34. A phased array ultrasound system provides additional spatial specificity via focused, electronically moveable ultrasound beams that can be reformed to follow patient movements or respond to physiological changes in the treatment volume.

Still referring to FIG. 2, array 32 is a specialized source of ultrasound energy and is based on multiple, electrically and acoustically separate ultrasound transducers 36 arranged in a two dimensional array such that each transducer 36 is driven separately by drivers 30. The transducers 36 are discrete elements, preferably constructed of a piezoelectric material, and the geometry and number of transducers 36 in array 32 can vary. Through use of controller 28, drivers 30, and phase detection subsystem 34, the phase of the ultrasound waves produced by each transducer 36 can be adjusted to form a highly focused ultrasound beam, generally designated at 42, which can be formed at a specific location within treatment volume 38. The beam 42 can be adjusted to compensate for acoustic aberrations and can be adjusted to follow movement of treatment volume 38. The focused location of ultrasound beam 42 is therefore determined by the phase distribution of all of transducers 36 of array 32. Preferably, array 32 is capable of generating ultrasonic waves at a frequency in the range of about 0.1–10 MHz. Further details of preferred therapeutic ultrasound system 24 can be found in commonly owned U.S. Pat. No. 5,590,657 issued to Cain et al., which is herein incorporated by reference in its entirety. However, it will be understood that other types of therapeutic ultrasound systems may be employed in practicing the method of the present invention.

Referring again to FIG. 2, diagnostic ultrasound system 26 generally includes a digital controller 44, a signal transmitter 46 and receiver 48 controlled by controller 44, a transmit/receive switch 50 to regulate the direction of signal flow, and a visual display 52. Through switch 50, transmitter 46 and receiver 48 communicate with an imaging transducer 54 to obtain image data for treatment volume 38. Preferably, imaging transducer 54 is capable of generating ultrasonic waves at a frequency in the range of about 2–10 MHz and is located as part of therapeutic ultrasound system 24 to allow diagnostic feedback for targeting and response to therapy. Of course, other configurations of diagnostic ultrasound system 24 may be implemented in conjunction with the present invention.

Figure 3:
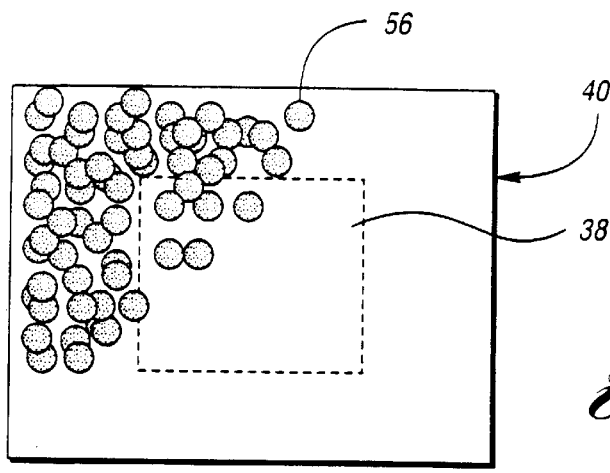
FIG. 3 is a schematic representation of providing microbubbles in a treatment volume.

FIGS. 3–8 provide schematic representations of the various stages of the method of the present invention. Referring first to FIG. 3, to create a surgical lesion in a treatment volume 38 of a patient 40, microbubbles 56 are provided in treatment volume 38. Microbubbles 56 may be introduced into the body in the form of a fluid, liquid droplets that subsequently vaporize, gas-filled bubbles, or other similar substance, such as conventional contrast agents. Microbubbles 56 are typically introduced into a patient 40 intravenously, and may either be injected systemically into the patient 40 or locally into the treatment volume 38. In the case where treatment volume 38 is an internal body or organ cavity surface, means would be provided for injecting microbubble-containing fluid into the cavity and for creating and maintaining a positive hydrostatic pressure. The apparatus would function to expand the lumen into a fluid filled volume so that all internal folds of the cavity would sufficiently admit the microbubbles. Alternatively, microbubbles 56 can be created in a selected treatment volume 38 using a high intensity ultrasound beam 42 from therapeutic ultrasound system 24. As one skilled in the art will recognize, widely varying amounts of microbubbles 56 may be provided in practicing the method of the present invention.

Figure 4:
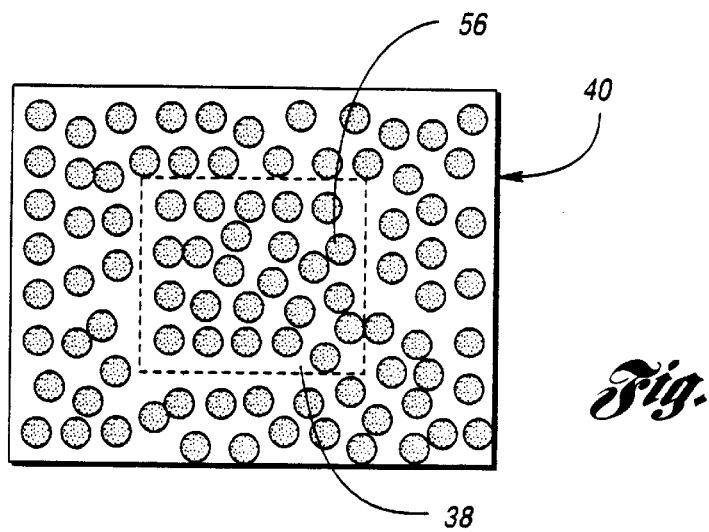
FIG. 4 is a schematic representation of the detection of microbubbles in the treatment volume.

Microbubbles 56 are preferably monitored with diagnostic ultrasound system 26 until their presence is detected in selected treatment volume 38, as shown in FIG. 4. In a preferred embodiment, more detailed information regarding microbubbles 56 is also determined at this stage. As is well known in the art, the emission of ultrasonic energy occurs at harmonics of the incident ultrasound frequency. Utilizing this property, harmonic imaging can show differences in microbubble populations more subtle than the presence or absence of microbubbles, for example, as described in U.S. Pat. No. 5,540,909 issued to Schutt. Harmonic imaging provides the opportunity for determining the particular size distribution of microbubbles 56 which are present in treatment volume 38. Using this information, the appropriate frequency of ultrasound beam 42 can be selected to subsequently cavitate that particular size distribution, and it may be determined if this frequency would be likely to produce collateral damage in the surrounding tissues.

In order to create a controlled lesion within treatment volume 38, the cavitation threshold for microbubbles 56 in treatment volume 38 is preferably lowered compared with the cavitation thresholds in an external volume 58, outside treatment volume 38. In the cases where microbubbles 56 are injected or created only in treatment volume 38, the cavitation threshold is already lowered in treatment volume 38 compared with external volume 58, since few, if any, microbubbles will exist in external volume 58. In instances where microbubbles 56 fill both treatment volume 38 and external volume 58, lowering of the cavitation threshold within treatment volume 38 can be accomplished in two different ways, as depicted in FIG. 5.

Figure 5A:
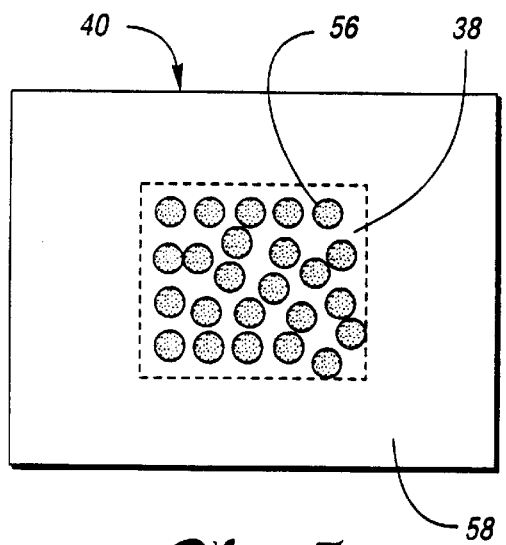
FIGS. 5a and 5b are schematic representations of the elimination of microbubbles from outside the treatment volume and the size tuning of microbubbles within the treatment volume, respectively, to lower the cavitation threshold of microbubbles in the treatment volume.

A first approach, shown in FIG. 5a, is to eliminate microbubbles 56 from external volume 58. At lower intensities, an ultrasound field will not violently collapse microbubbles 56, but rather will gently destabilize or otherwise eliminate the scattering of microbubbles 56 in a medium. Therefore, a low intensity ultrasound beam 42 from either diagnostic ultrasound system 26 or therapeutic ultrasound system 24 may be swept through external volume 58 to selectively eliminate microbubbles 56 therefrom, thereby isolating treatment volume 38 from surrounding tissues. As a result, treatment volume 38, with its preexisting microbubbles 56, will have a much lower threshold for cavitation than external volume 58 during subsequent lesion formation. During this step, as well as in subsequent steps involving cavitation and imaging, the selection of an appropriate ultrasound frequency will depend on both the location of treatment volume 38 and the resolution required for the procedure.

Figure 5B:
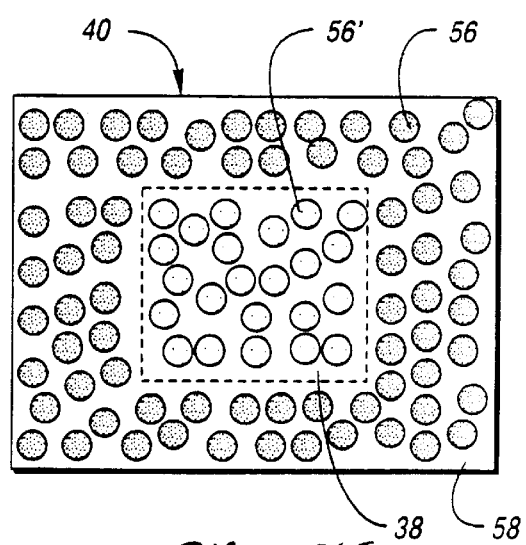

Alternatively, in the embodiment illustrated in FIG. 5b, a preliminary, high intensity ultrasound beam 42 from therapeutic ultrasound system 24 may be used to create a population of microbubbles 56' specific to treatment volume 38, and distinct from any microbubbles 56 within external volume 58. The population of microbubbles 56' can be made to have a narrow size distribution which is controlled by selection of the ultrasound frequency and drive amplitude. This limited size distribution has the effect of "tuning" microbubbles 56' to respond to a certain relatively narrow band of ultrasound frequencies. In a preferred embodiment, microbubbles 56' are tailored to oscillate at a low ultrasound frequency, at or below about 500 kHz. Therefore, an appropriate incident frequency for a subsequent ultrasound beam 42 can be chosen to oscillate microbubbles 56' at their maximal response frequency within treatment volume 38 for controlled lesion formation, without affecting microbubbles 56 in external volume 58 to the point of creating damage. The maximal response frequency may or may not correspond with linear resonance, since it is known that linear resonance is not the driving frequency of maximal response when using higher intensity fields. The above approach may be used in addition to providing microbubbles 56 exclusively into treatment volume 38, or in addition to the elimination of microbubbles 56 described with reference to FIG. 5a.

An important advantage of lowering the cavitation threshold in treatment volume 38 is that a low frequency ultrasound beam may be used in subsequent cavitation of microbubbles 56 or 56'. Since cavitation occurs more easily at low frequencies of ultrasound transmission, high frequency ultrasonic waves have typically been utilized during ultrasound procedures to avoid uncontrolled cavitation, even through high frequency ultrasound cannot penetrate through many bone interfaces and often excessively heats intervening tissues. By lowering the cavitation threshold in treatment volume 38 compared with external volume 58, the use of a low ultrasound frequency poses no threat of uncontrolled cavitation outside treatment volume 38. Therefore, a low ultrasound frequency, preferably at or below about 500 kHz, can be utilized which avoids tissue heating and possibly propagates through bone interfaces. The use of low frequencies allows therapeutic ultrasound system 24 to utilize larger phased array elements, significantly reducing array and driving system costs. Furthermore, the ultrasound field need not even be focused or localized if treatment volume 38 is the only volume containing microbubbles responsive to a low frequency, resulting in greatly simplified and less expensive systems which can penetrate into normally inaccessible regions of the body.

Figure 6A:
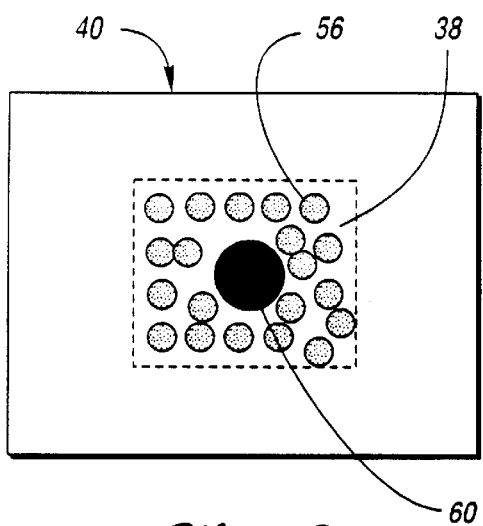
FIGS. 6a and 6b are schematic representations of two different methods of previewing the expected location of the surgical lesion within the treatment volume.

Before cavitation, ultrasound assembly 22 may be used to obtain a preview of the expected location of high intensity ultrasound beam 42 by affecting the microbubbles 56 at sub-lesion beam intensities. Starting from FIG. 5a, for example, an ultrasound beam 42 of low, sub-lesion intensity from therapeutic ultrasound system 24 is focused on treatment volume 38. The low intensity ultrasound beam 42 will gently destabilize microbubbles 56 at its focus, thereby removing the microbubbles 56 to leave a momentary dark spot 60, as depicted in FIG. 6a, on an image generated by the diagnostic ultrasound system 26. Dark spot 60 will indicate the expected location of the high intensity ultrasound beam 42. Perfusion of new blood into treatment volume 38 is then allowed so that microbubbles 56 can refill treatment volume 38 for predictable cavitation in subsequent lesion formation. Re-perfusion time of microbubbles 56 into treatment volume 38 might also indicate blood perfusion information useful for determining subsequent therapeutic protocols.

Figure 6B:
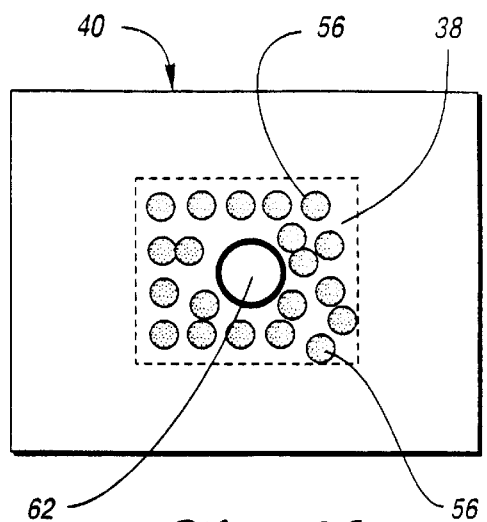

Instead of a low intensity ultrasound beam 42, a higher intensity ultrasound beam 42 from therapeutic ultrasound system 24 could be used for targeting the desired lesion location. As illustrated in FIG. 6b, a high intensity ultrasound beam 42 will cause increased cavitation, generating a bright spot 62, as opposed to dark spot 60, in the diagnostic image. If the high intensity ultrasound beam 42 is left on only briefly, a lesion will not form, but the expected location of the lesion within treatment volume 38 will be apparent. This alternative approach may be useful if microbubble collapse in the whole image field, rather than just within treatment volume 38, is observed at all obtainable low intensities.

Figure 7:
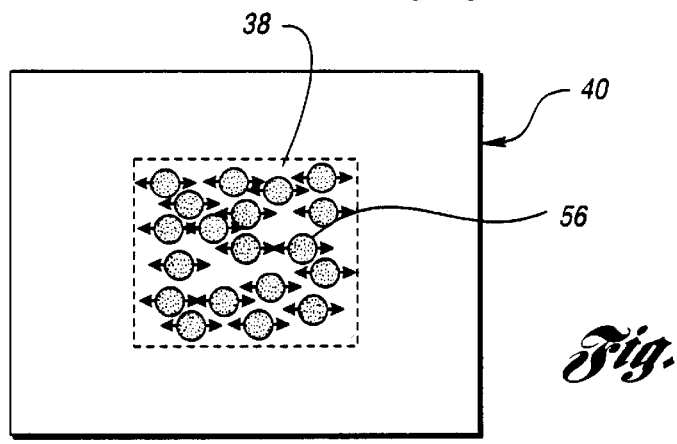
FIG. 7 is a schematic representation of the cavitation of microbubbles in the treatment volume to create the surgical lesion.

Once satisfied with the expected lesion location, microbubbles 56 in treatment volume 38 can be cavitated for lesion formation, as shown in FIG. 7. When treatment volume 38 comprises a surface of an internal body or organ cavity, the active region of fluid cavitation is the entire internal cavity surface or organ lining at the fluid tissue interface. By using the same phase information for every transducer element 36 of therapeutic ultrasound system 24 determined during the preview methods of either FIG. 6a or 6b, but by increasing all element drive amplitudes, the high intensity ultrasound beam 42 will focus at that same location for lesion formation. As described above, a low frequency ultrasound beam 42 may be used to cavitate microbubbles 56 to create the controlled surgical lesion. In the case depicted in FIG. 5b, where a tailored population of microbubbles 56' are created, the frequency of ultrasound beam 42 can be selected to correspond to the maximal response frequency of microbubbles 56' for optimal cavitation effects.

During cavitation, drugs or proto-pharmaceuticals can be delivered and activated within treatment volume 38, such as internal cavity or organ surfaces, using microbubbles 56. The drug reagents can be encapsulated within a microbubble using an encapsulation medium of a protein, a carbohydrate polymer, or a liposome. The encapsulated drugs are then activated or chemically modified through cavitation of microbubbles 56 at the specific tissue, organ, or region of interest. For example, a chemotherapeutic agent could be delivered directly in the tumor volume, or a blood-clotting drug could be delivered to the uterine surface for treatment of endometriosis. Using the method of the present invention, a relatively inert, and therefore safe, reagent can be injected via microbubbles 56 in high concentrations throughout the body, and then activated locally where its reactivity or cytotoxicity will only affect the region exposed to ultrasound. If the activated drugs are highly reactive and short-lived, then harmful accumulation in critical tissues such as the liver, bone marrow, and kidney is avoided.

However, the use of drug delivery in conjunction with the system and method of the present invention is not restricted to encapsulation of the drug reagents within the microbubble 56. In fact, the administration of drugs could be as simple as providing an admixture of microbubbles 56 and the drug, although the proximity of the drug and the cavitating microbubbles 56 is important. Molecular methods could also be used, such as conjugation of microbubbles to substances such as monoclonal antibodies or other molecules which bind to specific cells or otherwise accumulate or are targeted to specific tissues. Whether encapsulated or not, there are a number of biological effects which might be elicited by a therapeutic application of ultrasound using microbubbles 56 accompanied by drugs or other agents, for example, a reduction in post-lesion bleeding, an enhanced necrosis of cancer cells, and anti-inflammatory effects.

In addition, admixtures of microbubbles 56 comprising populations having different properties could be utilized with the system and method of the present invention. For instance, the response of a particular population of microbubbles 56 to low, typically diagnostic, ultrasound intensities compared with high, typically therapeutic, ultrasound intensities is of significance. Therefore, it would be beneficial to provide an admixture of microbubbles 56 having a first population that responds primarily to high intensity fields, and a second population that responds primarily to lower intensity fields and can be effectively eliminated from future high intensity applications.

Cavitation of microbubbles can produce temperatures and free radicals sufficient for free radical chemistry which can activate drugs or can create new biological substances from proto-pharmaceuticals. In addition, cavitation can have direct cellular effects. More particularly, the violent mechanical activity of cavitation can locally and temporarily disrupt cell membranes, resulting in uptake of substances such as drugs or DNA normally excluded therefrom. As with drugs, DNA can be included "naked" in the microbubble-containing fluid, within structures such as liposomes, or packaged within the microbubbles themselves. The packaging of DNA or a DNA/vector complex within cavitating microbubbles results in a mechanical "gene gun" to accomplish DNA delivery for gene therapy at specific tissue locations, avoiding unwanted and perhaps dangerous systemic DNA dispersion and uptake. For example, such specific DNA delivery to surface cells might be useful for treating excessive surface bleeding (e.g. of the uterus or bladder) or for treatment of uterine surfaces to prevent endometriosis.

Figure 8:
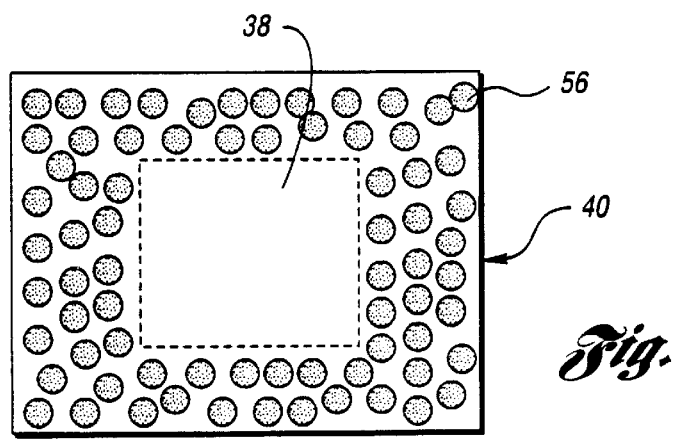
FIG. 8 is a schematic representation of the verification of lesion formation within the treatment volume at the expected lesion location.

Lastly, microbubbles 56 allow the verification of lesion formation after treatment volume 38 has been exposed to the high intensity ultrasound beam 42. Once a lesion has been obtained, all significant vasculature in that area will likely be destroyed since microbubbles 56 are restricted largely to blood vessels. Thus, as depicted in FIG. 8, following the introduction of new microbubbles 56 to the patient 40, treatment volume 38 will remain devoid of microbubbles 56 because there will be no blood flow to carry microbubbles 56 into treatment volume 38. The reintroduction of microbubbles 56 is monitored with diagnostic ultrasound system 26 and, depending on the results, further cavitation may be undertaken to achieve the desired lesion.

In conclusion, the method and assembly of the present invention use cavitation in a beneficial manner by creating a cavitation threshold in the treatment volume which is lower than cavitation thresholds in surrounding tissues. Cavitation thresholds are thus made predictable, a situation which almost never pertains in the body naturally, and the situation which has made cavitation a phenomenon to avoid in prior ultrasound procedures. As a result, low frequency ultrasound can be used to induce cavitation in the treatment without harming surrounding tissues, providing a distinct advantage over other methods of ultrasound surgery. The method and assembly of the present invention may be used for the localization and treatment of tumors or other malignant or nonmalignant masses in all soft tissue areas of clinical interest. With specific reference to uterine disorders, many hysterectomies could potentially be avoided through use of the noninvasive alternative offered by the assembly and method of the present invention.

It is understood, of course, that while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed.

What is claimed is:

1. A method for delivering substances to a selected treatment volume of a patient, the method comprising:
   providing a plurality of microbubbles in the treatment volume, wherein the microbubbles are associated with the substances to be delivered;
   expanding the treatment volume to fully admit the microbubbles therein; and
   cavitating the plurality of microbubbles with an ultrasound beam of sufficient energy at an appropriate frequency to deliver the substances in a controlled manner within the treatment volume.

2. The method of claim 1, wherein the treatment volume includes an internal body surface.

3. The method of claim 1, wherein the frequency of the ultrasound beam is a low frequency.

4. The method of claim 1, wherein the microbubbles have a threshold for cavitation, and wherein the method further comprises lowering the threshold for cavitation of the microbubbles in the treatment volume compared with the threshold for cavitation of microbubbles in a volume external to the treatment volume.

5. The method of claim 4, wherein lowering the threshold for cavitation of microbubbles in the treatment volume comprises producing a population of microbubbles within the treatment volume which have a limited size distribution, so that the microbubbles oscillate at a maximal response frequency.

6. The method of claim 4, wherein lowering the threshold for cavitation of microbubbles in the treatment volume comprises eliminating microbubbles from the external volume with a low intensity ultrasound beam.

7. The method of claim 1, wherein providing the plurality of microbubbles includes injecting the microbubbles into the patient systemically.

8. The method of claim 1, wherein providing the plurality of microbubbles includes injecting the microbubbles locally into the treatment volume.

9. The method of claim 1, further comprising detecting the presence of microbubbles in the treatment volume.

10. The method of claim 1 wherein the ultrasound beam is focused.

11. The method of claim 1, wherein the ultrasound beam is unfocused.

12. The method of claim 1, wherein cavitating the microbubbles disrupts cell membranes in the treatment volume, thereby enhancing the uptake of the delivered substances.

13. The method of claim 1, wherein the substances are encapsulated within the microbubbles, such that cavitating the microbubbles releases the substances into the treatment volume.

14. The method of claim 1, wherein the microbubbles are conjugated to the substances.

15. The method of claim 1, wherein the substances are provided in an admixture with the microbubbles.

16. The method of claim 1, wherein the substances include one of drugs and DNA.

17. An ultrasound assembly for delivering substances to a selected treatment volume of a patient, the assembly comprising:
   means for providing a plurality of microbubbles in the treatment volume, wherein the microbubbles are associated with the substances to be delivered;
   means for expanding the treatment volume to fully admit the microbubbles therein;
   a therapeutic transducer for generating and directing an ultrasound beam of energy in the treatment volume; and
   a controller for controlling the transducer so that the transducer generates and directs the ultrasound beam of sufficient energy at an appropriate frequency to deliver the substances in a controlled manner within the treatment volume.

18. The assembly of claim 17, wherein the treatment volume includes an internal body surface.

19. The ultrasound assembly of claim 17, wherein the frequency of the ultrasound beam is a low frequency.

20. The ultrasound assembly of claim 17, wherein the controller controls the therapeutic transducer to lower the threshold for cavitation of microbubbles in the treatment volume compared with the threshold for cavitation of microbubbles in a volume external to the treatment volume.

21. The ultrasound assembly of claim 17, wherein the ultrasound beam is focused.

22. The ultrasound assembly of claim 17, wherein the ultrasound beam is unfocused.

23. The ultrasound assembly of claim 17, wherein the therapeutic transducer comprises a plurality of transducer elements which form a phased array.

24. The ultrasound assembly of claim 17, wherein the therapeutic transducer is external to the body.

25. The ultrasound assembly of claim 17, wherein the therapeutic transducer is internal to the body.

26. The ultrasound assembly of claim 17, further comprising a diagnostic ultrasound system for providing images of the treatment volume.

27. The ultrasound assembly of claim 17, wherein the substances are encapsulated within the microbubbles.

28. The ultrasound assembly of claim 17, wherein the microbubbles are conjugated to the substances.

29. The ultrasound assembly of claim 17, wherein the substances are provided in an admixture with the microbubbles.

30. The ultrasound assembly of claim 17, wherein the substances include one of drugs and DNA.

31. A method for creating a surgical lesion in a selected treatment volume of a patient, the method comprising:
   injecting a plurality of microbubbles in the treatment volume;
   expanding the treatment volume to fully admit the microbubbles therein; and
   cavitating the plurality of microbubbles with an ultrasound beam of sufficient energy at an appropriate frequency to create the surgical lesion in a controlled manner within the treatment volume.

32. The method of claim 31, wherein the treatment volume includes an internal body surface.

33. An ultrasound assembly for creating a surgical lesion in a selected treatment volume of a patient, the assembly comprising:
    means for injecting a plurality of microbubbles in the treatment volume;
    means for expanding the treatment volume to fully admit the microbubbles therein;
    a therapeutic transducer for generating and directing an ultrasound beam of energy in the treatment volume; and
    a controller for controlling the transducer so that the transducer generates and directs the ultrasound beam of sufficient energy at an appropriate frequency to create the surgical lesion in a controlled manner within the treatment volume.

34. The assembly of claim 33, wherein the treatment volume includes an internal body surface.

35. A method for delivering substances to a selected treatment volume of a patient, the method comprising:
    providing a plurality of microbubbles in the treatment volume and in a volume external to the treatment volume, wherein the microbubbles are associated with the substances to be delivered, the microbubbles having a threshold for cavitation;
    controlling the microbubbles in the external volume to create a differential threshold for cavitation between the external volume and the treatment volume; and
    cavitating the plurality of microbubbles in the treatment volume with an ultrasound beam of sufficient energy at an appropriate frequency to deliver the substances in a controlled manner within the treatment volume.

36. The method of claim 35, wherein the treatment volume includes an internal body surface.

37. The method of claim 35, wherein the frequency of the ultrasound beam is a low frequency.

38. The method of claim 35, further comprising lowering the threshold for cavitation of microbubbles in the treatment volume by producing a population of microbubbles within the treatment volume which have a limited size distribution, so that the microbubbles oscillate at a maximal response frequency.

39. The method of claim 35, wherein controlling the microbubbles in the external volume includes reducing the cavitation potential in the external volume compared with the treatment volume.

40. The method of claim 39, wherein reducing the cavitation potential in the external volume comprises eliminating microbubbles from the external volume with a low intensity ultrasound beam.

41. The method of claim 35, further comprising expanding the treatment volume to fully admit the microbubbles therein.

42. The method of claim 35, wherein the substances are encapsulated within the microbubbles, such that cavitating the microbubbles releases the substances into the treatment volume.

43. The method of claim 35, wherein the microbubbles are conjugated to the substances.

44. The method of claim 35, wherein the substances are provided in an admixture with the microbubbles.

* * * * *